United States Patent [19]

Itoh et al.

[11] Patent Number: 5,228,899
[45] Date of Patent: Jul. 20, 1993

[54] HYDROXAMIC ACID ESTERS AND PLANT GROWTH REGULATION THEREWITH

[75] Inventors: Yoshikazu Itoh, Osaka; Akio Manabe, Hyogo; Masato Mizutani, Osaka; Naonori Hirata; Sachiko Uwayokote, both of Hyogo; Kazuo Izumi, Hyogo; Kenji Arai, Osaka, all of Japan

[73] Assignee: Sumitomo Chemical Company Limited, Osaka, Japan

[21] Appl. No.: 571,998

[22] Filed: Aug. 24, 1990

[30] Foreign Application Priority Data

Aug. 25, 1989 [JP] Japan ................................ 1-219083
Aug. 25, 1989 [JP] Japan ................................ 1-219084

[51] Int. Cl.$^5$ .................... C07C 69/612; C07C 83/10; A01N 31/24
[52] U.S. Cl. .................... 504/115; 560/312; 560/314; 562/442; 562/458; 548/452; 548/495; 548/542; 504/320; 504/309; 504/283; 504/2249.209; 504/319; 504/312; 504/335; 504/325; 504/285; 504/114; 504/287
[58] Field of Search ................ 560/312, 314; 562/458, 562/553, 510; 71/118, 114, 107; 504/318, 324

[56] References Cited

U.S. PATENT DOCUMENTS

| | | | |
|---|---|---|---|
| 3,183,255 | 5/1965 | Levy | 560/312 |
| 3,245,878 | 4/1966 | Berger et al. | 560/312 |
| 3,520,674 | 7/1970 | Neighbors | 71/111 |
| 3,642,805 | 2/1972 | Kistaludy et al. | 560/312 |
| 4,124,375 | 11/1978 | Bollinger et al. | 71/96 |
| 4,425,340 | 1/1984 | Teraji et al. | 424/246 |

FOREIGN PATENT DOCUMENTS 244786A 2/1987 European Pat. Off. .
0312763 4/1989 Fed. Rep. of Germany .

OTHER PUBLICATIONS

Effects of B-Alanine Analogues on Melanization and Catecholamine Levels, Istvan Ujvary et al., Insect Biochemistry, vol. 17, No. 3, pp. 389-399, 1987.
Amino-oxy Compounds: Part I-A New Route for the Synthesis of a-Amino-oxy Acids, K. S. Suresh et al., Indian Journal of Chemistry, vol. 10, Nov. 1972, pp. 1068-1069.

Primary Examiner—David B. Springer
Attorney, Agent, or Firm—Venable, Baetjer, Howard & Civiletti

[57] ABSTRACT

Plant growth regulators comprising, as an active ingredient, a substituted dicarboxylic acid derivative having the formula:

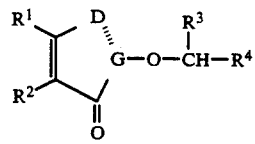

wherein $R^1$, $R^2$, $R^3$, $R^4$, D and G are the same as defined in the present specification, the substituted dicarboxylic acid derivatives, and processes for preparing the same, are disclosed. The plant growth regulators provided according to the present invention have a regulating activity on plant growth; more specifically, an action thereof of lowering the content of endogenous ethylene in a plant is utilized.

21 Claims, No Drawings

HYDROXAMIC ACID ESTERS AND PLANT GROWTH REGULATION THEREWITH

BACKGROUND OF THE INVENTION

1. Field of the Invention

The present invention relates to a plant growth regulator, more specifically to the utilizing of an action thereof of lowering the content of endogenous ethylene in a plant, which comprises a substituted dicarboxylic acid derivative, as an active ingredient, having the formula [I]:

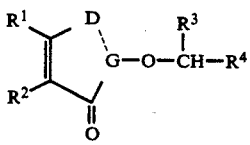

wherein $R^1$ and $R^2$ are, same or different, a hydrogen atom, a fluorine atom, a chlorine atom, a bromine atom, an iodine atom, a $C_1$-$C_3$ alkyl group or together represent a $C_3$-$C_5$ alkylene group or a divalent organic group represented by the formula, —CH=CH—CH=CH—, optionally substituted by $X_n$ to form a cyclic group; $R_3$ is a hydrogen atom or a $C_1$-$C_3$ alkyl group; $R_4$ is a cyano group or a group represented by the formula, —COOR$^5$, —CH$_2$COOR$^5$ or —CONR$^6$R$^7$; and D and G are a group represented by the formula, —COOR$^8$ or —CONR$^9$R$^{10}$, and N—H respectively with non-bonding, or are taken together to form CO—N, in which Xn is, same or different, a fluorine atom, a chlorine atom, a bromine atom, an iodine atom, a $C_1$-$C_4$ alkyl group, a $C_1$-$C_4$ alkoxy group, a hydroxyl group, a nitro group or an amino group, and n is 0, 1, 2, 3 or 4, $R^5$ is a hydrogen atom or a $C_1$-$C_6$ alkyl group, $R^6$ and $R^7$ are, same or different, a hydrogen atom, a $C_1$-$C_4$ alkyl group or together represent a $C_3$-$C_5$ alkylene group optionally substituted by a methyl group, $R^8$ is a hydrogen atom or a $C_1$-$C_6$ alkyl group, $R^9$ and $R^{10}$ are, same or different, a hydrogen atom, a $C_1$-$C_4$ alkyl group or together represent a $C_3$-$C_5$ alkylene group optionally substituted by a methyl group, and physiologically acceptable salts thereof, and an inert carrier or diluent.

2. Description of the Related Art

It is known that ethylene formed in a plant body promotes the aging of the plant, and if this aging can be inhibited, various possibilities arise; for example, an extension of the life of cut flowers and potted flowers, a prevention of the falling of the flowers and fruit of vegetables and fruit trees, and a regulation of the period of the maturity and an increase of the yield of fruit.

Accordingly, there is a strong demand for the development of a compound capable of lowering the content of endogenous ethylene in a plant and which can be utilized as a plant growth regulator.

As a result of intensive studies into solutions to the above problems, the present inventors found that a substituted dicarboxylic acid derivative having the formula [I] can be used as an active ingredient of a plant growth regulator, and thus accomplished the present invention.

SUMMARY OF THE INVENTION

According to the present invention, there are provided a plant growth regulator having an action of lowering the content of endogenous ethylene in a plant, and comprising, as an active ingredient, an effective amount of a substituted dicarboxylic acid derivative having the formula [I]:

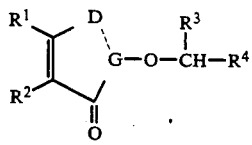

wherein $R^1$ and $R^2$ are, same or different, a hydrogen atom, a fluorine atom, a chlorine atom, a bromine atom, an iodine atom, a $C_1$-$C_3$ alkyl group or together represent a $C_3$-$C_5$ alkylene group or a divalent organic group represented by the formula, —CH=CH—CH=CH—, optionally substituted by Xn to form a cyclic group; $R_3$ is a hydrogen atom or a $C_1$-$C_3$ alkyl group; $R_4$ is a cyano group or a group represented by the formula, —COOR$^5$, —CH$_2$COOR$^5$ or —CONR$^6$R$^7$; and D and G are a group represented by the formula, —COOR$^8$ or —CONR$^9$R$^{10}$, and N—H respectively with non-bonding, or are taken together to form CO—N, in which Xn is, same or different, a fluorine atom, a chlorine atom, a bromine atom, an iodine atom, a $C_1$-$C_4$ alkyl group, a $C_1$-$C_4$ alkoxy group, a hydroxyl group, a nitro group or an amino group and n is 0, 1, 2, 3 or 4, $R^5$ is a hydrogen atom or a $C_1$-$C_6$ alkyl group, $R^6$ and $R^7$ are, same or different, a hydrogen atom, a $C_1$-$C_4$ alkyl group or together represent a $C_3$-$C_5$ alkylene group optionally substituted by a methyl group, $R^8$ is a hydrogen atom or a $C_1$-$C_6$ alkyl group, $R^9$ and $R^{10}$ are the same or different, a hydrogen atom, a $C_1$-$C_4$ alkyl group or together represent a $C_3$-$C_5$ alkylene group optionally substituted by a methyl group, or physiologically acceptable salts thereof, and an inert carrier or diluent. Further, there is provided a method of regulating plant growth by utilizing an action of the plant regulator of lowering the content of endogenous ethylene in a plant, which comprises applying an effective amount of a substituted dicarboxylic acid derivative having the formula [I]:

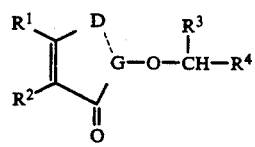

wherein $R^1$ and $R^2$ are, same or different, a hydrogen atom, a fluorine atom, a chlorine atom, a bromine atom, an iodine atom, a $C_1$-$C_3$ alkyl group or together represent a $C_3$-$C_5$ alkylene group or a divalent organic group represented by the formula, —CH=CH—CH=CH—, optionally substituted by Xn to form a cyclic group; $R_3$ is a hydrogen atom or a $C_1$-$C_3$ alkyl group; $R_4$ is a cyano group or a group represented by the formula, —COOR$^5$, —CH$_2$COOR$^5$ or —CONR$^6$R$^7$; and D and G are a group represented by the formula, —COOR$^8$ or —CONR$^9$R$^{10}$, and N—H respectively with non-bonding, or are taken together to form CO—N, in which Xn is, same or different, a fluorine atom, a chlorine atom, a bromine atom, an iodine atom, a $C_1$-$C_4$ alkyl group, a $C_1$-$C_4$ alkoxy group, a hydroxyl group, a nitro group or an amino group and n is 0, 1, 2, 3 or 4, $R^5$ is a hydrogen atom or a $C_1$-$C_6$ alkyl group, $R^6$ and $R^7$ are, same or different, a hydrogen atom, a $C_1$-$C_4$ alkyl group or together represent a $C_3$-$C_5$ alkylene group optionally substituted by a methyl group, $R^8$ is a hydrogen atom or a $C_1-C_6$ alkyl group, $R^9$ and $R^{10}$ are, same or different, a hydrogen atom, a $C_1-C_4$ alkyl group or together represent a $C_3-C_5$ alkylene group optionally substituted by a methyl group, or physiologically acceptable salts thereof, and an inert carrier or diluent to the plant.

Furthermore, there is provided a substituted dicarboxylic acid derivative having the formula:

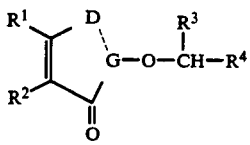  [II]

wherein $R^1$ and $R^2$ together represent a divalent organic group represented by the formula, —CH=CH—CH=CH—, to form a cyclic group; $R^3$ is a hydrogen atom or a $C_1-C_3$ alkyl group; $R^4$ is a cyano group or a group represented by the formula, —COOR$^5$, —CH$_2$COOR$^5$ or —CONR$^6$R$^7$; and D and G are a group represented by the formula, —COOR$^8$ or —CONR$^9$R$^{10}$, and N—H respectively with non-bonding, in which $R^5$ is a hydrogen atom or a $C_1-C_6$ alkyl group, $R^6$ and $R^7$, the same or different, a hydrogen atom, a $C_1-C_4$ alkyl group or together represent a $C_3-C_5$ alkylene group optionally substituted by a methyl group, $R^8$ is a hydrogen atom or a $C_1-C_6$ alkyl group, $R^9$ and $R^{10}$ are, same or different, a hydrogen atom, a $C_1-C_4$ alkyl group or together represent a $C_3-C_5$ alkylene group optionally substituted by a methyl group, or physiologically acceptable salts thereof and a method of production thereof;

a substituted dicarboxylic acid derivative having the formula [III]:

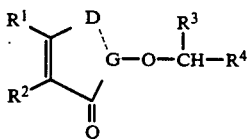  [III]

wherein $R^1$ and $R^2$ are, same or different, a hydrogen atom, a fluorine atom, a chlorine atom, a bromine atom, an iodine atom, a $C_1-C_3$ alkyl group or together represent a $C_3-C_5$ alkylene group or a divalent organic group represented by the formula, —CH=CH—CH=CH—, substituted by $X_n$ to form a cyclic group; $R^3$ is a hydrogen atom or a $C_1-C_3$ alkyl group; $R^4$ is a cyano group or a group represented by the formula, —COOR$^5$, —CH$_2$COOR$^5$ or —CONR$^6$R$^7$; and D and G are taken together to form CO—N, in which Xn is, same or different, a fluorine atom, a chlorine atom, a bromine atom, an iodine atom, a $C_1-C_4$ alkyl group, a $C_1-C_4$ alkoxy group, a hydroxyl group, a nitro group or an amino group and n is 1, 2, 3 or 4, $R^5$ is a hydrogen atom or a $C_1-C_6$ alkyl group, $R^6$ and $R^7$ are, same or different, a hydrogen atom, a $C_1-C_4$ alkyl group or together represent a $C_3-C_5$ alkylene group optionally substituted by a methyl group, or physiologically acceptable salts thereof and a method of production thereof;

a substituted dicarboxylic acid derivative having the formula [IV]:

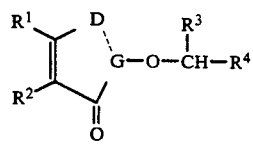  [IV]

wherein $R^1$ and $R^2$ are, same or different, a hydrogen atom, a fluorine atom, a chlorine atom, a bromine atom, an iodine atom, a $C_1-C_3$ alkyl group or together represent a $C_3-C_5$ alkylene group or a divalent organic group represented by the formula, —CH=CH—CH=CH—, substituted by Xn to form a cyclic group; $R^3$ is a hydrogen atom or a $C_1-C_3$ alkyl group; $R^4$ is a cyano group or a group represented by the formula, —CH$_2$COOR$^5$ or —CONR$^6$R$^7$; and D and G are a group represented by the formula, —COOR$^8$, and N—H respectively with non-bonding, in which Xn is, same or different, a fluorine atom, a chlorine atom, a bromine atom, an iodine atom, a $C_1-C_4$ alkyl group, a $C_1-C_4$ alkoxy group, a hydroxyl group, a nitro group or an amino group and n is 1, 2, 3 or 4, $R^5$ is a hydrogen atom or a $C_1-C_6$ alkyl group, $R^6$ and $R^7$ are, same or different, a hydrogen atom, a $C_1-C_4$ alkyl group or together represent a $C_3-C_5$ alkylene group optionally substituted by a methyl group, $R^8$ is a hydrogen atom or a $C_1-C_6$ alkyl group, or physiologically acceptable salts thereof and a method of production thereof;

a substituted dicarboxylic acid derivative having the formula [V]:

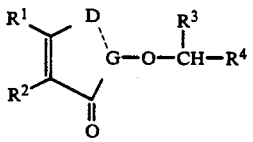  [V]

wherein $R^1$ and $R^2$ are, same or different, a hydrogen atom, a fluorine atom, a chlorine atom, a bromine atom, an iodine atom, a $C_1-C_3$ alkyl group or together represent a $C_3-C_5$ alkylene group or a divalent organic group represented by the formula, —CH=CH—CH=CH—, substituted by Xn so as to form a cyclic group; $R^3$ is a hydrogen atom or a $C_1-C_3$ alkyl group; $R^4$ is a cyano group or a group represented by the formula, —COOR$^5$, —CH$_2$COOR$^5$ or —CONR$^6$R$^7$; and D and G are a group represented by the formula, , —CONR$^9$R$^{10}$, and N—H respectively with non-bonding, or are taken together to form CO—N, in which Xn is, same or different, a fluorine atom, a chlorine atom, a bromine atom, an iodine atom, a $C_1-C_4$ alkyl group, a $C_1-C_4$ alkoxy group, a hydroxyl group, a nitro group or an amino group and n is 1, 2, 3 or 4, $R^5$ is a hydrogen atom or a $C_1-C_6$ alkyl group, $R^6$ and $R^7$ are, same or different, a hydrogen atom, a $C_1-C_4$ alkyl group or together represent a $C_3-C_5$ alkylene group optionally substituted by a methyl group, $R^9$ and $R^{10}$ are, same or different, a hydrogen atom, a $C_1-C_4$ alkyl group or together represent a $C_3-C_5$ alkylene group optionally substituted by a methyl group, or physiologically acceptable salts thereof and a method of production thereof;

a substituted dicarboxylic acid derivative having the formula [VI]:

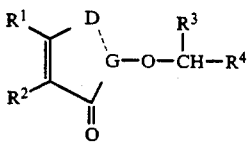

[VI]

wherein $R^1$ and $R^2$ are, same or different, a fluorine atom, a chlorine atom, a bromine atom, an iodine atom, a $C_1$-$C_3$ alkyl group or together represent a $C_3$-$C_5$ alkylene group to form a cyclic group; $R^3$ is a hydrogen atom or a $C_1$-$C_3$ alkyl group; $R^4$ is a group represented by the formula, —COOR$^5$; and D and G are a group represented by the formula, —COOR$^8$, and N—H respectively with non-bonding, in which $R^5$ is a hydrogen atom or a $C_1$-$C_6$ alkyl group, $R^8$ is a hydrogen atom or a $C_1$-$C_6$ alkyl group, or physiologically acceptable salts thereof and a method of production thereof;

a substituted dicarboxylic acid derivative having the formula [VII]:

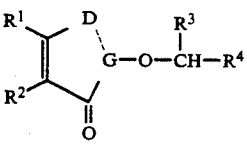

[VII]

wherein $R^1$ is hydrogen atom; $R^2$ is a fluorine atom, a chlorine atom, a bromine atom, an iodine atom or a $C_1$-$C_3$ alkyl group; $R^3$ is a hydrogen atom or a $C_1$-$C_3$ alkyl group; $R^4$ is a group represented by the formula, —COOR$^5$; and D and G are a group represented by the formula, —COOR$^8$, and N—H respectively with non-bonding, in which $R^5$ is a hydrogen atom or a $C_1$-$C_6$ alkyl group, $R^8$ is a hydrogen atom or a $C_1$-$C_6$ alkyl group, or physiologically acceptable salts thereof and a method of production thereof;

a substituted dicarboxylic acid derivative having the formula [VIII]:

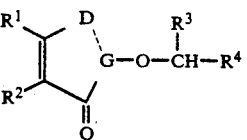

[VIII]

wherein $R^1$ is a fluorine atom, a chlorine atom, a bromine atom, an iodine atom, a $C_1$-$C_3$ alkyl group; $R^2$ is a hydrogen atom; $R^3$ is a hydrogen atom or a $C_1$-$C_3$ alkyl group; $R^4$ is a group represented by the formula, —COOR$^5$; and D and G are a group represented by the formula, —COOR$^8$, and N—H respectively with non-bonding, in which $R^5$ is a hydrogen atom or a $C_1$-$C_6$ alkyl group, $R^8$ is a hydrogen atom or a $C_1$-$C_6$ alkyl group, or physiologically acceptable salts thereof and a method of production thereof.

DESCRIPTION OF THE PREFERRED EMBODIMENTS

Hereinafter, the present invention is explained in detail.

Among the plant growth regulators of the present invention, those wherein $R^1$ and $R^2$ are, same or different, a hydrogen atom, a fluorine atom, a chlorine atom, a $C_1$-$C_3$ alkyl group or together represent a $C_3$-$C_5$ alkylene group or a divalent organic group represented by the formula, —CH=CH—CH=CH—, optionally substituted by Xn to form a cyclic group; $R^3$ is a hydrogen atom or a $C_1$-$C_3$ alkyl group; $R^4$ is a cyano group or a group represented by the formula, —COOR$^5$ or —CH$_2$COOR$^5$; and D and G are a group represented by the formula, —COOR$^8$ or —CONR$^9$R$^{10}$, and N—H respectively with non-bonding, or are taken together to form CO—N, in which Xn is, same or different, a fluorine atom, a chlorine atom, a bromine atom, an iodine atom, a $C_1$-$C_4$ alkyl group, a $C_1$-$C_4$ alkoxy group, a hydroxyl group, a nitro group or an amino group and n is 0, 1, 2, 3 or 4, $R^5$ is a hydrogen atom or a $C_1$-$C_4$ alkyl group, $R^8$ is a hydrogen atom or a $C_1$-$C_4$ alkyl group, $R^9$ and $R^{10}$ are, same or different, a hydrogen atom or a $C_1$-$C_3$ alkyl group , or physiologically acceptable salts thereof, are preferred from the view point of efficiency. As examples of the physiologically acceptable acid addition salt, there are known metal salts such as sodium and potassium or amine salts such as ammonium and amine and the like. More preferred are those wherein $R^1$ and $R^2$ are, same or different, a hydrogen atom, a chlorine atom, a $C_1$ alkyl group or together represent a $C_4$ alkylene group or a divalent organic group represented by the formula, —CH=CH—CH=CH—, optionally substituted by Xn to form a cyclic group; $R^3$ is a hydrogen atom or a $C_1$ alkyl group; $R^4$ is a cyano group or a group represented by the formula, —COOR$^5$ or —CH$_2$COOR$^5$; and D and G are a group represented by the formula; —COOR$^8$ or —CONR$^9$R$^{10}$, and N—H respectively with non-bonding, or are taken together to form CO—N, in which Xn is, same or different, a fluorine atom, a chlorine atom, a $C_1$ alkyl group, a $C_1$ alkoxy group, a hydroxyl group or a nitro group and n is 0, 1, 2, 3 or 4, $R^5$ is a hydrogen atom or a $C_1$-$C_4$ alkyl group, $R^8$ is a hydrogen atom or a $C_1$-$C_2$ alkyl group, $R^9$ and $R^{10}$ are, same or different, a hydrogen atom or a $C_1$-$C_2$ alkyl group, or physiologically acceptable salts thereof.

Further, particularly more preferred are those wherein $R^1$ and $R^2$ are, same or different, a hydrogen atom, a chlorine atom, a $C_1$ alkyl group or together represent a $C_4$ alkylene group or a divalent organic group represented by the formula, —CH=CH—CH=CH—, optionally substituted by Xn to form a cyclic group; $R^3$ is a hydrogen atom or a $C_1$ alkyl group; $R^4$ is a cyano group or a group represented by the formula, —COOR$^5$; and D and G are a group represented by the formula, —COOR$^8$ and N—H respectively with non-bonding, or are taken together to form CO—N, in which Xn is, same or different, a fluorine atom, a chlorine atom, a $C_1$ alkyl group, a $C_1$ alkoxy group or a hydroxyl group, and n is 0 or 1, $R^5$ is a hydrogen atom or a $C_1$-$C_2$ alkyl group, $R^8$ is a hydrogen atom or a $C_1$-$C_2$ alkyl group, and physiologically acceptable acid addition salts thereof; the most preferred being those wherein $R^1$ and $R^2$ are, same or different, a chlorine atom, a $C_1$ alkyl group or a divalent organic group represented by the formula, —CH=CH—CH=CH—, to form a cyclic group; $R^3$ is a hydrogen atom or a $C_1$ alkyl group; $R^4$ is a cyano group or a group represented by the formula, —COOR$^5$; and D and G are a group represented by the formula, —COOR$^8$, and N—H respectively with non-bonding, or are taken together to form CO—N, in which $R^5$ is a hydrogen atom or a $C_1$ alkyl group, $R^8$ is a hydrogen atom or a $C_1$-$C_2$ alkyl group, or physiologically acceptable salts thereof.

The plant growth regulator of the present invention can be used for various flowers; for example, carnations (*Dianthus caryophyllus* L.), sweet peas (*Lathyrus odoratus* L.), thunberg lilies (*Lilium elegans* Thunb.), *Aconitum napellus*, butterfly weeds (*Asclepias tuberosa* L.), Virginia lions' hearts (*Physostegia virginiana*), rocket larkspurs (*Delphinium ajacis* L.), herb tree mallows (*Lavatera trimestris* L.), campanula L. bellflowers flowers such as canterbury bells (*Campanula medium* L.), clustered bells (*Campanula glomerate* L.), and willow bells (*Campanula persicifolia* L.), bleeding hearts (*Dicentra spectabilis* DC.), speed wells (Veronica L.), scarlet plume euphorbias (*Euphorbia fulgens*), alstroemerias (*Alstroemeria x hybrida*), freesias (*Freesia x hybrida* L.H. Bailey), sweet williams (*Dianthus babatus* L.), common snapdragons (*Antirrhinum majus* L.), sweet scabious (*Scabiosa causasica*), stocks (*Matthiola incana* R.Br.), babys-breathes (*Gypsophila paniculata* L.) bougainvilleas (Bougainvillea Comm.), fish geraniums (*Pelargonium x hortorum* L.H. Bailey), calceolaria (*Calceolaria x hybrida* Hort), Orchidaceae orchids such as cattleya (*Cattleya x hydrida*), cymbidiums (*Cymbidium x hydrida*), lady's slippers (*Paphiopedilum x hydrida*), dendrobium (Dendrobium Swartz), moth orchids (*Phalaenopsis x hydrida*) and dancing-lady orchids (*Oncidium swartz*), bouvardias (Bouvardia Salisb), sea lavenders (Limonium Mill), gloly lilies (Glorisa L.), cosmoses (Cosmos Cav.), russell prairie gentians (*Eustoma russellianum* G. Don), dahlias (*Dahlia x cultorum* Thorser et Reis), fuchsias (Fuchsia L.), and Chinese ixora (*Ixora chinese* Lam.), but are not limited thereto. The plant growth regulator can sufficiently lower the content of endogenous ethylene in a plant without causing serious phytotoxicity of the flower. Namely, the plant growth regulator of the present invention can induce an action of lowering the content of endogenous ethylene in a plant and maximize the longevity of cut flower, without causing undesirable side-effects to the plant.

The process for preparing the substituted dicarboxylic acid derivatives and physiologically acceptable acid addition salts thereof used as an active ingredient in plant growth regulator of the present invention is explained as follows.

(1) Among the compounds, a compound having the formula [I] wherein D and G are taken together to form CO—N; i.e. an imido derivative having the formula [IX]:

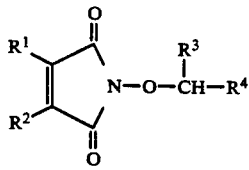

wherein $R^1$, $R^2$, $R^3$ and $R^4$ are each as defined above, are obtainable by reacting a substituted anhydride having the formula [X]:

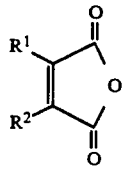

wherein $R^1$ and $R^2$ are each as defined above, with a substituted hydroxylamine derivative having the formula [XI]:

wherein $R^3$ and $R^4$ are each as defined above.

If necessary, the reaction may be conducted in the presence of a reaction assistant such as sodium acetate, 4-(dimethyl amino) pyridine, and acetic anhydride, and is usually carried out at a temperature of from 0° C. to 200° C., for 0.1-24 hours.

The amounts of the reagents used in the reaction are 1-1.2 equivalents of the hydroxylamine derivative having the formula [XI] and/or 0.001-5 equivalents of the reaction assistant to one equivalent of the substituted anhydride having the formula [X].

The reaction is usually conducted in the presence or absence of a solvent. The solvents are, for example, chloroform and 1,2-dichloroethane.

After the reaction is completed, the reaction mixture is subjected to usual post-treatments such as extraction with an organic solvent, concentration, filtration, neutralization and demineralization to give the desired substituted compound having the formula [I] wherein D and G are taken together to form CO—N. If necessary, the product is further subjected to chromatography and recrystallization, etc., to purify the same.

The substituted anhydride having the formula [X] as one starting material is commercially available, and can be prepared from the corresponding dicarboxylic acid by known methods. The hydroxylamine derivative having the formula [XI] as the other starting material is commercially available, and can be prepared by a process disclosed in Bull. Soc. Chim. France, 834 (1976), or the like.

(2) Among the compounds, a compound having the formula [I] wherein D and G are taken together to form CO—N, i.e., an imido derivative having the formula [IX]:

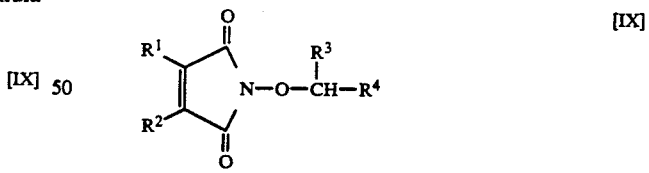

wherein $R^1$, $R^2$, $R^3$ and $R^4$ are each as defined above, are obtainable by reacting a substituted N-hydroxyimido derivative having the formula [XII]:

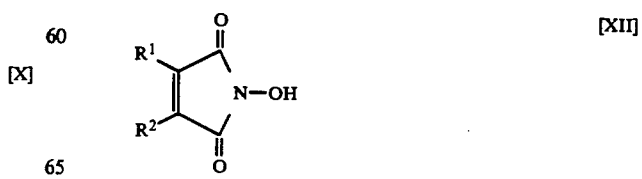

wherein $R^1$ and $R^2$ are each as defined above, with a compound having the formula [XIII]:

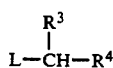 [XIII]

wherein L is a fluorine atom, a chlorine atom, a bromine atom, an iodine atom, a methane sulfonyloxy group or a tosyloxy group; $R^3$ and $R^4$ are each as defined above.

If necessary, the reaction may be conducted in the presence of a reaction assistant.

As the reaction assistant, there may be used inorganic bases such as sodium hydroxide, potassium hydroxide and potassium carbonate, etc., and organic bases such as triethylamine, pyridine, and N,N-diethylaniline, etc.

The reaction is usually carried out at the temperature from 0° C. to 200° C., for 0.1-24 hours.

The amounts of the reagents used in the reaction are 1-1.5 equivalents of the compound having the formula [XIII] and/or 1-2 equivalents of the reaction assistant to one equivalent of the substituted N-hydroxyimido derivative having the formula [XII].

The reaction is usually conducted in the presence or absence of a solvent. The solvents are, for example, dimethylformamide (DMF), dimethylsulfoxide (DMSO), water and mixtures thereof.

After the reaction is completed, the reaction mixture is subjected to usual post-treatments such as extraction with an organic solvent, concentration, filtration, neautralization and demineralization to give the desired substituted compound having the formula [I] wherein D and G are taken together to form CO—N. If necessary, the product is further subjected to chromatography, and recrystallization, etc., to purity the same.

The substituted N-hydroxyimido derivative having the formula [XII] as one starting material is commercially available, and can be prepared from the corresponding anhydride by known methods. The compound having the formula [XIII] as the other starting material is commercially available, and can be prepared by known methods.

(3) Among the compounds, a compound having the formula [I] wherein D and G are a group represented by the formula, —COOR⁸ or —CONR⁹R₁₀, and N—H respectively with non-bonding, i.e., a substituted dicarboxylic acid derivative having the formula [XIV] or [XV]:

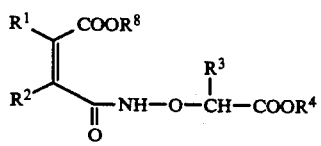 [XIV]

or

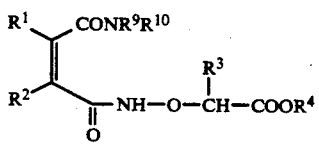 [XV]

wherein $R^1$, $R^2$, $R^3$, $R^4$, $R^8$, $R^9$ and $R^{10}$ are each as defined above, are obtainable by reacting the present compound having the formula [I] wherein D and G are taken together to form CO—N, i.e., an imido derivative having the formula [IX]

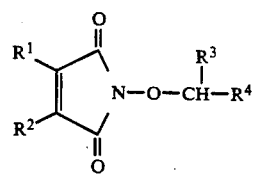 [IX]

wherein $R^1$, $R^2$, $R^3$, and $R^4$ are each as defined above, with a metal hydroxide having the formula [XVI]:

MOH [XVI]

wherein M is a metal atom, a metal alkoxide having the formula [XVII]:

$R^{81}OM$ [XVII]

wherein $R^{81}$ is a $C_1$-$C_6$ alkyl group; M is a metal atom, or a amine having the formula [XVIII]:

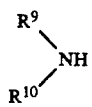 [XVIII]

wherein $R^9$ and $R^{10}$ are each as defined above, in the presence of solvent.

Examples of the solvent are water, alcohols such as methanol and ethanol, etc., halogenated hydrocarbons such as methylene chloride and chloroform, etc., ethers such as ethyl ether and tetrahydrofuran (THF), etc., and hydrocarbons such as toluene and benzene, etc.

The reaction is usually carried out at the temperature of from 0° C. to 100° C. for 1-48 hours.

The amounts of the reagents used in the reaction are 1-2 equivalents of a metal hydroxide having the formula [XVI], a metal alkoxide having the formula [XVII], or a amine having the formula [XVIII] to one equivalents of the imido derivative having the formula [IX].

After the reaction is completed, the mixture is subjected to usual post-treatments such as extraction with an organic solvent, concentration, filtration, neutraliztion, demineralization and recrystallization, etc., to give the desired compound having the formula [I] wherein D and G are a group represented by the formula, —COOR⁸ or —CONR⁹R¹⁰, and N—H respectively with non-bonding.

(4) Among the compounds, a physiologically acceptable acid addition salt of a compound having the formula [I] wherein $R^1$, $R^2$, $R^3$, D and G are each as defined above; $R^4$ is a group represented by the formula, —COOR⁵; $R^5$ is a hydrogen atom, i.e., an acid addition salt of a compound having the formula [IXX]:

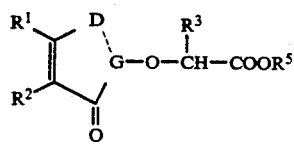 [IXX]

or wherein $R^1$, $R^2$, $R^3$ and $R^4$ are each as defined above; D and G are a group represented by the —COOR⁸ and N—H respectively with non-bonding; $R^8$ is a hydrogen atom, i.e., an acid addition salt of a compound having the formula [XX]:

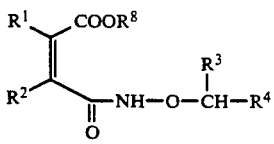

are obtainable by reacting the corresponding acid with a base.

The bases are, for example, metal hydrides such as sodium hydride and potassium hydride, etc., metal hydroxides such as sodium hydroxide and potassium hydroxide, etc., and organic bases such as triethylamine, pyridine and N,N-diethylaniline, etc.

If necessary, the reaction may be conducted in the presence of solvent.

Examples of the solvent are water, alcohols such as methanol and ethanol, etc., halogenated hydrocarbons such as methylene chloride and chloroform, etc., ethers such as ethyl ether and tetrahydrofuran (THF), etc., and hydrocarbons such as toluene and benzene, etc.

(5) Among the compounds, an acid having the formula [IXX] or [XX] as defined in (4) is obtainable by reacting the corresponding acid addition salt with an acid.

The acids are, for example, organic acids such as trifluoroacetic acid and p-toluenesulfonic acid, etc., and mineral acids such as hydrochloric acid and sulfuric acid, etc.

If necessary, the reaction may be conducted in the presence of solvent.

Examples of the solvents are water, alcohols such as methanol and ethanol, etc., halogenated hydrocarbons such as methylene chloride and chloroform, etc., and ethers such as ethyl ether and tetrahydrofuran (THF), etc.

Further, a compound obtained by such the above processes also can be converted to an analog thereof, by a conventional process (for example, hyrolysis of the t-buty ester with frifuoroacetic acid, conversion of the carboxylic acid to a metal salt thereof, or acid amidation of the carboxylic acid.)

Typical examples of the compound contained in the plant growth regulator, which can be prepared through the above procedures, are shown in Table 1.

TABLE 1

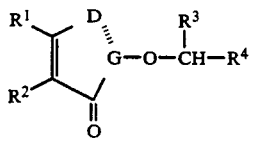

| D | G | R$^1$ | R$^2$ | R$^3$ | R$^4$ |
|---|---|---|---|---|---|
| CON | | H | H | H | COOH |
| CON | | H | H | H | COOCH$_3$ |
| CON | | CH$_3$ | H | H | COOC$_2$H$_5$ |
| CON | | CH$_3$ | CH$_3$ | H | COOH |
| CON | | CH$_3$ | CH$_3$ | CH$_3$ | COOH |
| CON | | CH$_3$ | CH$_3$ | H | COOCH$_3$ |
| CON | | CH$_3$ | CH$_3$ | H | COOC$_4$H$_{9\text{-}t}$ |
| CON | | CH$_3$ | CH$_3$ | H | COONa |
| CON | | CH$_3$ | CH$_3$ | H | COO$^\ominus$(C$_2$H$_5$)$_3$$^\oplus$NH |
| CON | | C$_2$H$_5$ | C$_2$H$_5$ | H | COOCH$_3$ |
| CON | | iso-C$_3$H$_7$ | H | H | CON(C$_2$H$_5$)$_2$ |
| CON | | CH$_3$ | CH$_3$ | H | CN |
| CON | | F | F | H | COOCH$_3$ |
| CON | | Cl | Cl | H | COOH |
| CON | | Br | Br | CH$_3$ | COOC$_2$H$_5$ |
| CON | | I | I | H | COOH |
| CON | | Cl | H | H | COOCH$_3$ |
| CON | | Br | F | H | COOCH$_3$ |
| CON | | CH$_2$CH$_2$CH$_2$CH$_2$ | | H | COOCH$_3$ |
| CON | | CF=CH—CH=CH | | H | COOC h |
| CON | | CH=CF—CH=CH | | CH$_3$ | COOC$_3$H$_{7\text{-}iso}$ |
| CON | | CF=CF—CH=CH | | H | COOC$_4$H$_{9\text{-}n}$ |
| CON | | CF=CH—CH=CF | | H | COOH |
| CON | | CH=CF—CF=CH | | H | COOK |
| CON | | CF=CCl—CH=CH | | H | COOH |
| CON | | CF=CH—CCl=CH | | H | COOC$_3$H$_{7\text{-}n}$ |
| CON | | CCl=CH—CH= | | H | COOCH$_3$ |
| CON | | CH=CCl—CH=CH | | CH$_3$ | COOH |
| CON | | CCl=CCl—CH=CH | | H | COONa |
| CON | | CCl=CH—CH=CCl | | H | COOC$_4$H$_{9\text{-}t}$ |
| CON | | CH=CCl—CCl=CH | | H | COOH |
| CON | | CCl=CCl—CCL=CCl | | CH$_3$ | COOC$_2$H$_5$ |
| CON | | CBr=CH—CH=CH | | H | COOH |
| CON | | CH=CBr—CH=CH | | H | COOCH$_3$ |
| CON | | CI=CH—CH=CH | | iso-C$_3$H$_7$ | COOH |
| CON | | CH=CI—CH= | | H | COOCH$_3$ |
| CON | | C(NO$_2$0=CH—CH=CH | | H | COOC$_2$H$_5$ |
| CON | | CH=C(NO$_2$)—CH=CH | | H | COOH |
| CON | | C(OH)=CH—CH=CH | | H | COOH |
| CON | | CH=C(OH)—CH=CH | | H | COOC$_2$H$_5$ |
| CON | | C(CH$_3$)=CH—CH=CH | | CH$_3$ | COOH |
| CON | | CH=C(C$_2$H$_5$)—CH=CH | | H | COONa |
| CON | | C(C$_4$H$_{9\text{-}t}$)=CH—CH=CH | | H | COOC$_2$H$_5$ |

TABLE 1-continued $$\underset{R^2}{\overset{R^1}{\diagdown}}C=\underset{\underset{O}{\parallel}}{C}-G-O-\underset{\overset{|}{R^3}}{CH}-CH-R^4$$

| D | G | R¹ | R² | R³ | R⁴ |
|---|---|---|---|---|---|
| CON | | C(OCH₃)=CH—CH=CH | | CH₃ | COOH |
| CON | | C(OC₂H₃)=CH—CH=CH | | H | COOCH₃ |
| CON | | CH=C(OC₄H₉-sec)—CH=CH | | H | CONH₂ |
| CON | | C(NH₂)=CH—CH=CH | | CH₃ | COOCH₃ |
| CON | | CH=C(NH₂)—CH=CH | | H | COOC₂H₅ |
| CON | | CH=C(NH₂)—CH=CH | | H | CON⟨C₅H₁₀⟩ |
| COOH | NH | CH₃ | CH₃ | H | COOH |
| COOK | NH | CH₃ | H | H | COOK |
| COONa | NH | H | H | CH₃ | COOCH₃ |
| COOCH₃ | NH | CH₃ | CH₃ | H | COOH |
| COOCH₃ | NH | CH₃ | CH₃ | H | COONa |
| COOCH₃ | NH | CH₃ | CH₃ | H | COOCH₃ |
| CON(C₂H₅)₂ | NH | CH₃ | CH₃ | CH₃ | COO⁻(C₂H₅)₂⁺NH₂ |
| CONH₂ | NH | CH₃ | H | C₂H₅ | CN |
| CONHCH₃ | NH | CH₃ | H | H | CONHCH₃ |
| COOH | NH | F | F | H | COOH |
| COOH₃ | NH | Cl | Cl | CH₃ | COOCH₃ |
| COOH | NH | Br | Br | H | COOCH₃ |
| COONa | NH | I | I | H | COONa |
| COOC₂H₅ | NH | H | F | H | COOCH₅ |
| COOH | NH | Cl | H | H | COOH |
| COOH | NH | Br | H | H | CONHCH₃ |
| CON(C₂H₅)₂ | NH | F | Br | H | COOC₂H₅ |
| COOH | NH | I | Cl | H | COOH |
| COOCH₃ | NH | CH₃ | CH₃ | H | COOH |
| COOCH₃ | NH | CH₃ | H | H | COOK |
| COOCH₃ | NH | H | CH₃ | CH₃ | COOCH₃ |
| CON(C₂H₅)₂ | NH | CH₃ | CH₃ | H | COOH |
| CONH₂ | NH | CH₃ | CH₃ | H | COONa |
| CONHCH₃ | NH | CH₃ | CH₃ | H | COOCH₃ |
| COOH | NH | CH₃ | CH₃ | CH₃ | COO⊖(C₂H₅)₂⊕NH₂ |
| COOK | NH | CH₃ | H | C₂H₅ | CN |
| COOH | NH | CH=CH—CH=CH | | H | COOH |
| COOK | NH | CH=CH—CH=CH | | CH₃ | COOK |
| COOCH₃ | NH | CH=CH—CH=CH | | H | COOCH₃ |
| CONH₂ | NH | CH=CH—CH=CH | | H | CONH₂ |
| COONa | NH | CH=CH—CH=CH | | H | COOCH₃ |
| CON(CH₃)₂ | NH | CH=CH—CH=CH | | H | COOC₂H₅ |
| CON⟨C₅H₁₀⟩ | NH | CH=CH—CH=CH | | H | CN |
| COOC₂H₅ | NH | C(NO₂)=CH—CH=CH | | H | COOC₂H₅ |
| COOH | NH | CH=CH—CH=C(NO₂) | | H | COOH |
| COOCH₃ | NH | CH=CF(NO₂)—CH=CH | | H | COOCH₃ |
| COOC₂H₅ | NH | CH=CH—C(NO₂)=CH | | H | COOC₂H₅ |
| COOC₂H₅ | NH | CCl=CH—CH=CH | | H | COOC₂H₅ |
| COOCH₃ | NH | CH=CH—CH=CCl | | CH₃ | COOCH₃ |
| CONH₂ | NH | CH=CCl—CH=CH | | H | CONH₂ |
| COONa | NH | CH=CH—CCl=CH | | CH₃ | COONa |
| COOC₂H₅ | NH | CF=CH—CH=CH | | H | COOC₂H₅ |
| CONH₂ | NH | CH=CF—CH=CH | | CH₃ | CONH₂ |
| COOCH₃ | NH | CH=CH—CF=CH | | H | COOCH₃ |
| COOK | NH | CH=CH—CH=CF | | C₂H₅ | COOK |
| COOH | NH | CBr=CH—CH=CH | | H | COOH |
| COOCH₃ | NH | CH=CBr—CH=CH | | H | COONa |
| COOC₂H₅ | NH | CH=CH—CBr=CH | | H | COOC₂H₅ |
| COOH | NH | CH=CH—CH=CBr | | H | COOH |
| COOH | NH | CI=CH—CH=CH | | H | COOH |
| COOCH₃ | NH | CH=CI—CH=CH | | H | COOH |
| COOCH₃ | NH | CH=CH—CI=CH | | H | COONa |
| COOC₂H₅ | NH | CH=CH—CH=CI | | H | COOH |
| COOH | NH | C(OH)=CH—CH=CH | | CH₃ | COOH |

TABLE 1-continued

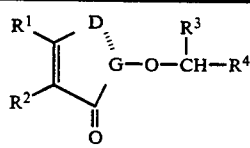

| D | G | R¹ | R² | R³ | R⁴ |
|---|---|---|---|---|---|
| COOCH$_3$ | NH | CH=(OH)—CH=CH | | H | COOCH$_3$ |
| COOC$_2$H$_5$ | NH | CH=CH—C(OH)=CH | | H | COOH |
| COOH | NH | CH=CH—CH=C(OH) | | H | COOH |
| COOH | NH | C(CH$_3$)=CH—CH=CH | | H | COOH |
| COOCH$_3$ | NH | CH=C(C$_2$H$_5$)—CH=CH | | H | COOCH$_3$ |
| COOC$_2$H$_5$ | NH | CH=CH—C($_{iso}$C$_3$H$_7$)=CH | | CH$_3$ | COOC$_2$H$_5$ |
| COOC$_4$H$_{9-n}$ | NH | CH=CH—CH=C(C$_4$H$_{9-t}$) | | CH$_3$ | COOH |
| COOH | NH | C(OCH$_3$)=CH—CH=CH | | H | COOH |
| COOCH$_3$ | NH | CH=C(OCH$_3$)—CH=CH | | H | COOCH$_3$ |
| COOC$_2$H$_5$ | NH | CH=CH—C(OC$_2$H$_5$)=CH | | CH$_3$ | COOC$_2$H$_5$ |
| COONa | NH | CH=CH—CH=C(OC$_3$H$_{7ios}$) | | CH$_3$ | COONa |

The substituted dicarboxylic acid derivative can be utilized as an active ingredient of plant growth regulators used for various purposes; for example, an extension of the life of cut flowers and potted flowers, a prevention of the falling of flowers and fruit of vegetables and fruit trees, and a regulation of the period of the maturity and an increase of the yield of fruits.

A method of preserving cut flowers utilizing the invention can be easily carried out without the need for a special treatment; for example, by only immersing the cut ends of cut flowers in an aqueous solution of a substituted dicarboxylic acid derivative having the formula [I].

Representative examples of the presentation method include a method of maintaining the freshness of cut flowers by keeping the flowers immersed in the above aqueous solution, and a method which comprises immersing cut flowers therein for a predetermined time and maintaining their freshness after the immersion. As the former method there is known, for example, a posttreatment such as that wherein cut flowers are sold by a store while kept in a vessel such as a bucket, or that wherein cut flowers are arranged in a vase in a home or at an exhibition. As the latter method, there is known, for example, a pretreatment wherein a producer carries out a treatment with the chemical for a predetermined time such as 4, 12, and 24 hours, etc., after the flowers are harvested, and then delivers the flowers. Namely, this invention can be utilized in many cases.

The present plant growth regulator is further described in detail below, taking the use for the preservation of cut flowers as an example.

When a substituted dicarboxylic acid derivative having the formula [I] is used as a cut flower-preserving agent, the concentration thereof cannot be definitely described due to changes therein according to various conditions such as the kind of flower to be used as an object, but is usually about 1 to about 2000 ppm, preferably about 2 to about 1000 ppm in the posttreatment described above, or about 20 to about 2000 ppm in the pretreatment described above, more preferably about 6 to 600 ppm in the posttreatment, or 20 to 2000 ppm in the pretreatment for 4-12 hours and 20 to 600 ppm in the pretreatment for 24 hours.

The compounds of the present invention are usually used in the form of an aqueous solution. The aqueous solution can also contain a proper surfactant or polar solvent such as ethanol.

Specific examples of the surfactant include alkylbenzenesulfonic acid salts, higher alcohol sulfuric acid ester salts, alkyltrimethylammonium chlorides, betaine type surfactants, sodium laulyl sulfates, naphthalene sulfonate formaldehyde condensate, polyoxyethylene sorbitan monooleates, polyoxyethylene styrylphenyl ethers, polyoxyethylene lauryl ethers, polyoxyethylene nonylphenyl ethers, polyoxyethylenepolyoxypropylene block polymers, and sucrose fatty acid esters. When the surfactant is used with an active ingredient of the plant growth regulator, the concentration thereof is usually 3 to 1000 ppm in the pretreatment or 3 to 300 ppm in the posttreatment, although this depends on the kind of surfactants, kind of plants, form of formulations, treatment time, and methods of application.

Known substances also can be mixed with the aqueous solution; for example, nutrients such as nitrogen, phosphoric acid, potassium, and sucrose; micronutrients such as iron, zinc, manganese, copper, and boron; and plant growth regulators such as B-Nine and benzyladenine.

The present invention will be explained in more detail by the following synthesis examples, formulation examples and test examples, which is no way limit the present invention.

SYNTHESIS EXAMPLE 1

To a solution of 0.65 g of 2,3-dimethylmaleic anhydride in 20 ml of 1,2-dichloroethane was added 0.5 g of sodium acetate, 0.85 g of methoxy carbonyl methoxyamine hydrochloride, and 0.74 g of 4-(dimethylamino)-pyridine, and the mixture was heated for 3 hours under refluxing. After the reaction was completed, the reaction mixture was left to stand for cooling, and thereafter, 50% of 5% aqueous hydrochloric acid was added to the mixture, which was then extracted with 50 ml of chloroform. The organic layer was washed with 30 ml an aqueous solution of sodium hydrogen carbonate and then with 30 ml of an aqueous solution of sodium chloride, dried over magnesium sulfate, and concentrated to give 1.06 g of N-(methoxy-carbonylmethoxy)-2,3-dimethylmaleimido (Compound (1)).

M.P. 89°

$^1$H-NMR (CDCl$_3$, TMS)

δ(ppm) 1.96 (s, 6H), 3.76 (s, 3H), 4.64 (s, 2H)

SYNTHESIS EXAMPLE 2

To a solution of 1.08 g of N-hydroxy-2,3-dimethylmaleimido in 5 ml of dimethylformamide (DMF) was added a solution of 0.34 g of sodium hydroxide in 1 ml of water while cooling with ice, and to the mixed solution was added dropwise 1.57 g of tert.-butylbromoacetate while cooling with ice, followed by stirring at the same temperature for 1.5 hours. After the reaction was completed, the reaction mixture was filtered on a glass filter, the residue was washed with cold water and then cold diisopropylether, and dried to give 0.90 g of N-(t-buthoxy carbonylmethoxy)-2,3-dimethylmaleimide (Compound (2)).

M.P. 95° C.

$^1$H-NMR (CDCl$_3$, TMS)

δ(ppm) 1.47 (s, 9H), 1.94 (s, 6H), 4.52 (s, 2H)

SYNTHESIS EXAMPLE 3

To a suspension of 5 g of N-(carboxylmethoxy) phthalimide in 40 ml of water was added 24 ml of an aqueous solution of potassium hydroxide (1N), followed by stirring at room temperature over night. After the reaction was completed, the resultant solution was concentrated to remove water under a reduced pressure, to give 5.3 g of mono potassium N-(2-carboxyl) benzoyl aminooxy acetate Compound (33) in the form of white crystals having a physical property of deliquescence.

$^1$H-NMR (D$_2$O, external standard TMS)

δ(ppm) 4.45 (s, 2H), 7.35-7.85 (m, 4H)

SYNTHESIS EXAMPLE 4

To a solution of 2 g of N-(carboxylmethoxy) phthalimide in 50 ml of methanol was added dropwise 1.74 g of a methanol solution of sodium methoxide (28%). After the reaction was completed, the resultant solution was concentrated to remove methanol under a reduced pressure, to give 2.48 g of sodium N-(2-methoxy carbonyl) benzoyl aminooxy acetate (Compound (28)) in the form of white crystals.

M P. 80°-85° C.

$^1$H-NMR (D$_2$O, external standard TMS)

δ(ppm) 4.06 (s, 3H), 4.60 (s, 2H), 7.62-8.15 (m, 4H)

SYNTHESIS EXAMPLE 5

To a solution of 2.5 g of N-(ethoxy carbonyl methoxy) phthalimide in 30 ml of methylene chloride was added 1 g of diethylamine at room temperature, followed by reacting for 3 hours under refluxing. After the reaction was completed, the reaction mixture was poured into 100 ml of cold aqueous hydrochloric acid, the resultant mixture was obtained from the organic layer and extracted with ethy acetate from the water layer, and the obtained resultant mixture was dried over magnesium sulfate, and filtrated. The filtrate was concentrated under a reduced pressure, and the residue was purified by silica gel column chromatography (elution solvent; hexane:ethylacetate=1:1, v/v) to obtain 1.5 g of N-(2-diethylamino carbonyl)benzoyl aminooxy ethyl acetate as a yellowish viscous oily substance (Compound (30)).

$^1$H-NMR (CDCl$_3$, TMS)

δ(ppm) 0.93-1.16 (t, 3H), 1.16-1.39 (t, 3H), 1.19-1.43 (t, 3H), 2.96-3.31 (q, 2H), 3.39-3.74 (q, 2H), 4.07-4.43 (q, 2H), 4.50 (s, 2H), 7.11-7.86 (m, 4H), 7.11-7.86 (m, 1H)

SYNTHESIS EXAMPLE 6

To a solution of 500 mg of N-(carboxymethoxy)-2,3-dimethylmaleimide (Compound (4)) in 20 ml of tetrahydrofuran (THF) was added a solution of 100 mg of an oily sodium hydride (60%) at room temperature, and the mixture was stirred for half an hour. After the reaction was completed, the resultant mixture was concentrated to remove the solvent, under a reduced pressure, and 50 ml of hexane was added to the residue followed by stirring. The obtained precipitate was filtered, and dried under a reduced pressure to give 540 mg of sodium salt of N-(carboxymethoxy)-2,3-dimethylmaleimide (Compound (5)) in the form of white crystals.

M.P. 280° C. (dec.)

$^1$H-NMR(D$_2$O, external std. TMS) δ(ppm) 1.90(S,6H), 4.45(S,2H)

SYNTHESIS EXAMPLE 7

To a solution of 1 g of sodium N-(2-methoxycarbonyl) benzoylaminooxyacetate (Compound (28)) in 50 ml methanol was added dropwise 0.5 g of trifluoroacetic acid, and the mixture was stirred for 10 minutes. After the reaction was completed, the resultant mixture was concentrated to remove the solvent under a reduced pressure, and 30 ml of water was added to the residue, which was then extracted with diethylether. The organic layer was dried over magnesium sulfate, and concentrated to give 0.3 g of N-(2-methoxycarbonyl) benzoyl aminooxyacetate (Compound (29)) in the form of white crystals.

M.P. 143°-145° C. (dec.)

$^1$H-NMR (CbCl$_3$, TMS) 3.72(S,3H), 4.65(S,2H), 7.30-8.10(m,4H)

SYNTHESIS EXAMPLE 8

To a solution of 2.77 g of N-(t-butoxy carbonylmethoxy) phthalimide (Compound (13)) in 10 ml of anhydrous methylene chloride was added dropwise 1.37 g of trifluoro acetic acid, and the mixture was followed by stirring at room temperature over night. After the reaction was completed, the resultant was filtrated to give 520 mg of N-(corboxy methoxy) phthalimide (Compound (11)) in the form of white crystals.

M.P. 205° C.

$^1$H-NMR (DMSO-d$_6$, TMS)

δ (ppm) 4.71 (S,2H), 7.81 (S,4H)

MS(m/e, 70ev).

221(Mt), 147, 105, 77

Examples of the present invention prepared in the same manner as above, and the substituted dicarboxylic acid derivative having the plant growth regulating activity, are shown in Table 2 and Table 3.

TABLE 2

$$\underset{R^2}{\overset{R^1}{>}}C=C\underset{\underset{O}{\|}}{\overset{D}{<}}\underset{C}{\overset{}{\underset{\|}{C}}}G-OCH\underset{R^4}{\overset{R^3}{<}}$$

| Compound No. | D | G | R¹ | R² | R³ | R⁴ | physical properties | ¹H-NMR δ (ppm) |
|---|---|---|---|---|---|---|---|---|
| (1) | | CON | CH₃ | CH₃ | H | COOCH₃ | white crystal m.p. 89° C. | (CDCl₃, TMS) 1.96(s, 6H), 3.76(s, 3H), 4.64(s, 2H) |
| (2) | | CON | CH₃ | CH₃ | H | COOC₄H₉-t | white crystal m.p. 95° C. | (CDCl₃, TMS)1.47(s, 9H), 1.94(s, 6H), 4.52(s, 2H) |
| (3) | | CON | CH₃ | CH₃ | H | COOC₂H₅ | white crystal m.p. 57° C. | (CDCl₃, TMS)1.19–1.42(t, 3H), 1.99(s, 6H), 4.08–4.43(q, 2H), 4.65(s, 2H) |
| (4) | | CON | CH₃ | CH₃ | H | COOH | white crystal m.p. 118° C. | (CDCl₃, TMS)2.01(s, 6H), 4.71(s, 2H), 9.22(s, 1H) |
| (5) | | CON | CH₃ | CH₃ | H | COONa | white crystal m.p. 280° C. (dec.) | (D₂O, external std. TMS) 1.90(s, 6H), 4.45(s, 2H) |
| (6) | | CON | CH₃ | CH₃ | CH₃ | COOCH₃ | white crystal m.p. 74° C. | (CDCl₃, TMS)1.52–1.63(d, 3H), 1.99(s, 6H), 3.80(s, 3H), 4.55–4.90(q, 2H) |
| (7) | | CON | CH₃ | H | H | COOC₂H₅ | yellowish viscous oily substance | (CDCl₃, TMS)1.18–1.41(t, 3H), 2.10(s, 3H), 4.07–4.41(q, 2H), 4.64(s, 2H), 6.31(s, 1H) |
| (8) | | CON | Cl | Cl | H | COOC₂H₅ | white crystal m.p. 94° C. | (CDCl₃, TMS)1.18–1.42(t, 3H), 4.07–4.41(q, 2H), 4.67(s, 2H) |
| (9) | | CON | CH₃ | CH₃ | H | CN | white crystal | (CDCl₃, TMS)2.00(s, 6H), 4.83(s, 2H) |
| (10) | | CON | CH₂CH₂CH₂CH₂ | | H | COOCH₃ | white crystal m.p. 111–114° C. | (CDCl₃, TMS)1.56–1.90(m, 4H), 2.16–2.64(m, 4H), 3.77(s, 3H), 4.75(s, 2H) |
| (11) | | CON | CH=CH–CH=CH | | H | COOH | white crystal m.p. 187° C. (dec.) | (DMSO-α₆, TMS)4.67(s, 2H), 7.75(s, 4H) |
| (12) | | CON | CH=CH–CH=CH | | H | COONa | white crystal m.p. 200° C. (dec.) | (D₂O, external std. TMS) 4.45(s, 2H), 7.70(s, 4H) |
| (13) | | CON | CH=CH–CH=CH | | H | COOC₄H₉-t | white crystal m.p. 148° C. | (CDCl₃, TMS)1.51(s, 9H), 4.70(s, 2H), 7.78(s, 4H) |
| (14) | | CON | CH=CH–CH=CH | | H | COOCH₃ | white crystal m.p. 145° C. | (CDCl₃, TMS)3.80(s, 3H), 4.76(s, 2H), 7.73(s, 4H) |
| (15) | | CON | CH=CH–CH=CH | | H | COOC₂H₅ | white crystal m.p. 100° C. | (CDCl₃, TMS)1.18–1.41(t, 3H), 4.04–4.40(q, 2H), 4.76(s, 2H), 7.73(s, 4H) |
| (16) | | CON | CH=CH–CH=CH | | H | CN | white crystal | (DMSO-d₆, TMS)5.12(s, 2H), 7.75(s, 4H) |
| (17) | | CON | CH=CH–CH=CH | | H | CH₂COOC₂H₅ | white crystal | (CDCl₃, TMS)1.09–1.32(t, 3H), 2.47–2.68(t, 2H), 4.04–4.26 (t, 2H), 4.09–4.29(t, 2H), 7.70(s, 4H) |
| (18) | | CON | CH=CH–CH=CH | | CH₃ | COOC₂H₅ | white crystal m.p. 70° C. | (CDCl₃, TMS)1.15–1.37(t, 3H), 1.56–1.67(d, 3H), 4.04–4.41 |

TABLE 2-continued

| Compound No. | D | G | R¹ | R² | R³ | R⁴ | physical properties | ¹H-NMR δ (ppm) |
|---|---|---|---|---|---|---|---|---|
| (19) | | CON | CH=CH—CH=CH | | CH₃ | COOCH₃ | white crystal m.p. 65° C. | q, 2H), 4.67–4.99(q, 1H), 7.60(s, 4H)<br>(CDCl₃, TMS)1.61–1.70(d, 3H), 3.79(s, 3H), 4.71–5.05(q, 2H), 7.85(s, 4H) |
| (20) | | CON | C(NO₂)=CH—CH=CH | | H | COOC₂H₅ | white crystal m.p. 92° C. | (CDCl₃, TMS)1.19–1.43(t, 3H), 4.07–4.45(q, 2H), 4.83(s, 2H), 7.95–8.31(m, 3H) |
| (21) | | CON | CH=C(NO₂)—CH=CH | | H | COOC₂H₅ | white crystal m.p. 149° C. | (CDCl₃, TMS)1.19–1.43(t, 3H), 4.08–4.44(q, 2H), 4.82(s, 2H), 7.99–8.14(m, 1H), 8.54–8.74 (m, 2H) |
| (22) | | CON | CH=CCl—CH=CH | | H | COOC₂H₅ | white crystal m.p. 107° C. | (CDCl₃, TMS)1.18–1.42(t, 3H), 4.09–4.45(q, 2H), 4.78(s, 2H), 7.75–7.80(m, 3H) |
| (23) | | CON | CCl=CCl—CCl=CCl | | H | COOC₂H₅ | white crystal m.p. 184° C. | (CDCl₃, TMS)1.19–1.43(t, 3H), 4.11–4.48(q, 2H), 4.81(s, 2H) |
| (24) | | CON | C(OH)=CH—CH=CH | | H | COOC₂H₅ | white crystal | (CDCl₃, TMS)1.18–1.41(t, 3H), 4.08–4.45(q, 2H), 4.79(s, 2H), 5.85–6.47(m, 1H), 7.12–7.64 (m, 3H) |
| (25) | | CON | C(OCH₃)=CH—CH=CH | | H | COOC₂H₅ | white crystal m.p. 108° C. | (CDCl₃, TMS)1.18–1.41(t, 3H), 4.01(s, 3H), 4.07–4.43(q, 2H), 4.76(s, 2H), 7.16–7.84(m, 3H) |
| (26) | | CON | CH=C(CH₃)—CH=CH | | H | COOC₂H₅ | white crystal m.p. 78° C. | (CDCl₃, TMS)1.16–1.39(t, 3H), 2.47(s, 2H), 4.05–4.42(q, 2H), 4.75(s, 2H), 7.40–7.76(m, 3H) |
| (27) | | CON | CF=CH—CH=CH | | H | COOC₂H₅ | white crystal m.p. 78° C. | (CDCl₃, TMS)1.17–1.42(t, 3H), 4.09–4.94(q, 2H), 4.78(s, 2H), 7.24–7.95(m, 3H) |
| (28) | COOCH₃ | NH | CH=CH—CH=CH | | H | COONa | white crystal m.p. 80–85° C. | (D₂O, external std. TMS) 4.06(s, 3H), 4.60(s, 2H), 7.62–8.15(m, 4H) |
| (29) | COOCH₃ | NH | CH=CH—CH=CH | | H | COOH | white crystal m.p. 143–145° C. (dec.) | (CDCl₃, TMS)3.72(s, 3H), 4.65(s, 2H), 7.30–8.10(m, 4H) |
| (30) | CON(C₂H₅)₂ | NH | CH=CH—CH=CH | | H | COOC₂H₅ | yellowish viscous oily substance | (CDCl₃, TMS)0.93–1.16(t, 3H), 1.16–1.39(t, 3H), 1.19–1.43 (t, 3H), 3.96–3.31(q, 2H), 3.39–3.74(q, 2H), 4.07–4.43 (q, 2H), 4.50(s, 2H), 7.11–7.86 (m, 4H), 7.11–7.86 (m, 1H) |

TABLE 2-continued
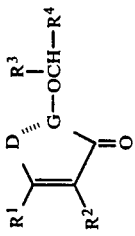
| Compound No. | D | G | R$^1$ | R$^2$ | R$^3$ | R$^4$ | physical properties | $^1$H-NMR δ (ppm) |
|---|---|---|---|---|---|---|---|---|
| (31) | COOC$_2$H$_5$ | NH | C(NO$_2$)=CH—CH=CH CH=CH—CH=C(NO$_2$) | H | H | COOC$_2$H$_5$ | mixture of isomers orange resinous material | (CDCl$_3$, TMS)1.03–1.35(t, 3H), 1.25–1.48(t, 3H), 3.96–4.40 (q, 2H), 4.20–4.53(q, 2H), 4.52(s, 2H), 7.53–8.30(m, 3H) |
| (32) | COOC$_2$H$_5$ | NH | CH=C(NO$_2$)—CH=CH CH=CH—C(NO$_2$)=CH | H | H | COOC$_2$H$_5$ | mixture of isomers light yellowish crystal | (CDCl$_3$, TMS)1.08–1.41(t, 3H), 1.30–1.52(t, 3H), 4.06–4.41 (q, 2H), 4.21–4.56(q, 2H), 4.58(s, 2H), 7.58–8.78(m, 3H) |

TABLE 3

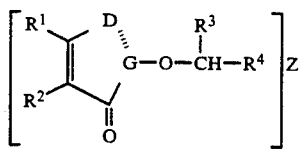

| Compound No. | D | G | R¹ | R² | R³ | R⁴ | Z | physical properties | $^1$H-NMR δ (ppm) |
|---|---|---|---|---|---|---|---|---|---|
| (33) | COO⁻ | NH | CH=CH—CH=CH | H | COO⁻ | | K⁺, H⁺ | white crystal deliquescence | (D₂O, external std. TMS) 4.45(s, 2H), 7.35-7.85(m, 4H) |
| (34) | COO⁻ | NH | CH=CH—CH=CH | H | COO⁻ | | Na⁺, H⁺ | white crystal m.p. 110-115° C. colorless | (D₂O, external std. TMS) 4.45(s, 2H), 7.35-7.86(m, 4H) |
| (35) | COO⁻ | NH | CH=CH—CH=CH | H | COO⁻ | | (C₂H₅)₃⁺NH, H⁺ | kesinous material | (D₂O, external std. TMS) 1.17-1.42(t, 9H), 3.03-3.37 (q, 2H), 4.5(s, 2H), 7.48-7.98(m, 2H) |

The following are formulation examples wherein the compounds of the present invention used are indicated by the numbers given in Table 2, Table 3, and the synthesis examples. Note, all parts are by weight.

FORMULATION EXAMPLE 1

Fifty parts of each of the compounds of the present invention (1)–(35), 5 parts of sodium lauly sulfate, and 45 parts of synthetic hydrated silicon dioxide were thoroughly pulverized and mixed to obtain a wettable powder containing an active ingredient concentration of 50%.

FORMULATION EXAMPLE 2

Forty parts of each of the compounds of the present invention (3), (20) or (27), 2 parts of sodium laulyl sulfate, 2 parts of dinaphthylmethanedisulfonate, 14 parts of kaolin clay, and 20 parts of synthetic hydrated silicon dioxide are thoroughly pulverized and mixed to obtain a wettable powder containing an active ingredient concentration of 40%.

FORMULATION EXAMPLE 3

Two parts of each of the compounds of the present invention (3), (12), (15) and (33), 2 parts of sodium laulyl sulfate, 30 parts of bentonite, and 65 parts of kaolin clay were thoroughly pulverized and mixed, well kneaded with water, and then granulated and dried to obtain a granule containing an active ingredient concentration of 2%.

FORMULATION EXAMPLE 4

Twenty five parts of each of the compounds of the present invention (9), (26), (28) and (35), 3 parts of polyoxyethylene sorbitan monooleate, 3 parts of carboxyl methyl cellulose (CMC), and 69 parts of water are mixed and wet-pulverized to form particles having a size of not more than 5 microns, to thereby obtain a suspension formulation containing an active ingredient concentration of 25%.

FORMULATION EXAMPLE 5

Ten parts of each of the compounds of the present invention (33), (34) and (35), 1 part of polyoxyethylenestyrylphenylether, and 89 parts of water were mixed to obtain a liquid containing an active ingredient concentration of 10%.

The effect of the compounds of the present invention as an active ingredient of a plant growth regulator will be shown by the following test examples. The compounds of the present invention used are indicated by the compound number given in Table 2, Table 3 and the synthesis examples.

TEST EXAMPLE 1

Test of Inhibition of Ethylene Formation

First, on the 6th day after sowing, 10 sections (each 10 mm) of hypocotyls of mung bean (Phaseolus aureus) were added to 0.5 ml of 50 mM potassium phosphate buffer solution (pH 6.8) containing 1 mM indoleacetic acid and a test compound, in a screw bottle. The bottle was then sealed with a silicone stopper, and after culturing in the dark at 30° C. for 4 hours, the quantity of ethylene formed was detected by gas chromatography.

The results are shown as a ratio of inhibition of ethylene biosynthesis in Table 4.

TABLE 4

| Compound No. | Concentration (ppm) | Inhibition rate of ethylene formation (%) |
|---|---|---|
| (1) | 200 | 100 |
| | 20 | 96 |
| (2) | 200 | 68 |
| (3) | 200 | 93 |
| (4) | 200 | 100 |
| (5) | 200 | 100 |
| (6) | 200 | 88 |
| (7) | 200 | 79 |
| (10) | 200 | 98 |
| | 20 | 95 |
| (11) | 200 | 95 |
| (12) | 200 | 86 |
| (13) | 200 | 98 |
| (14) | 200 | 100 |
| | 20 | 89 |
| (15) | 200 | 100 |
| | 20 | 92 |
| (16) | 200 | 61 |
| (17) | 200 | 66 |
| (18) | 200 | 90 |
| (19) | 200 | 88 |
| (21) | 200 | 73 |
| (22) | 200 | 92 |
| (24) | 200 | 88 |
| (25) | 200 | 91 |
| (26) | 200 | 93 |
| (27) | 200 | 93 |
| (28) | 200 | 94 |
| (29) | 200 | 88 |
| (30) | 200 | 50 |
| (33) | 200 | 96 |
| (34) | 200 | 94 |
| without | — | 0 |

TABLE 4-continued

| Compound No. | Concentration (ppm) | Inhibition rate of ethylene formation (%) |
|---|---|---|
| chemical | | |

TEST EXAMPLE 2

Test of Maintenance of Freshness of Carnations

Three carnations (cultivar: Nora) were arranged in aqueous solutions of test compounds each having a concentration of 2% sucrose, and preserved in a growth room at 25° C. Then, 7 days after the treatment, the freshness of each flower was observed.

The freshness was evaluated according to the following criteria.
A: fresh
B: beginning to wither
C: withered and fading
D: dead
The results are shown in Table 5.

| Compound No. | Concentration (ppm) | Evaluation |
|---|---|---|
| (1) | 200 | AAA |
| | 60 | AAA |
| (2) | 200 | ABB |
| (3) | 200 | AAA |
| | 60 | AAA |
| (4) | 200 | AAA |
| | 60 | AAA |
| (5) | 200 | AAA |
| | 60 | AAA |
| (6) | 200 | AAA |
| | 60 | AAA |
| (7) | 200 | AAA |
| | 60 | AAA |
| (8) | 200 | AAA |
| | 60 | AAA |
| (9) | 200 | AAA |
| | 60 | AAA |
| (10) | 200 | AAA |
| (11) | 200 | AAA |
| | 60 | AAA |
| (12) | 200 | AAA |
| | 60 | AAA |
| (14) | 200 | AAA |
| | 60 | AAA |
| (15) | 200 | AAA |
| | 60 | AAA |
| (16) | 200 | AAA |
| | 60 | AAA |
| (17) | 200 | AAA |
| (18) | 200 | AAA |
| | 60 | AAA |
| (19) | 200 | AAA |
| | 60 | AAA |
| (21) | 200 | AAA |
| (22) | 200 | AAA |
| | 60 | AAA |
| (24) | 200 | AAA |
| | 60 | AAA |
| (25) | 200 | AAA |
| | 60 | AAA |
| (26) | 200 | AAA |
| | 60 | AAA |
| (27) | 200 | AAA |
| | 60 | AAA |
| (28) | 200 | AAA |
| | 60 | AAA |
| (29) | 200 | AAA |
| | 60 | AAA |
| (32) | 200 | AAC |
| (33) | 200 | AAA |
| | 60 | AAA |
| (34) | 200 | AAA |
| | 60 | AAA |

-continued

| Compound No. | Concentration (ppm) | Evaluation |
|---|---|---|
| without any chemical | — | CDD |

TEST EXAMPLE 3

Test of Phytotoxicity of Carnations

Five carnations (cultivar: Nora) were arranged in aqueous solutions of test compounds each having a concentration of 300 ppm Triton X-100, and preserved in a growth room at 25° C. After the treatment for 12 hours, the cut flowers were rearranged in 800 ml of distilled water. Then, 9 days after the treatment, the freshness and the severity of the phytotoxicity of each flower were observed. The compound used for comparison is shown in Table 6.

TABLE 6

| Compounds | Chemical formula | Note |
|---|---|---|
| A | $NH_2OCH_2COOH$ | Commercially available compound |

The freshness was evaluated according to the following evaluation criteria.
A: fresh
B: beginning to wither
C: withered and fading
D: dead The severity of phytotoxicity to test plants was expressed according to the following 4 ratings.
− No phytotoxicity observed.
± Slight phytotoxicity observed.
+ Weak phytotoxicity observed.
++ Strong phytotoxicity observed.
The results are shown in Table 7.

TABLE 7

| Test compound | Concentration (ppm) | Freshness | Phytotoxicity |
|---|---|---|---|
| (33) | 2000 | A | — |
| A | 2000 | B | ++ |

The substituted dicarboxylic acid derivatives having the formula [I] inhibit the formation of ethylene in plant bodies, and thus are useful as an active ingredient of plant growth regulators having various uses such as the maintenance of the freshness of cut flowers without causing serious phytotoxicity of the flowers.

We claim:

1. A plant growth regulator comprising, as an active ingredient, a substituted dicarboxylic acid derivative having the formula:

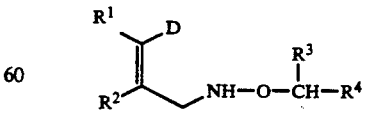

wherein $R^1$ and $R^2$ are, same or different, a hydrogen atom, a fluorine atom, a chlorine atom, a bromine atom, an iodine atom, a $C_1$-$C_3$ alkyl group or together represent a $C_3$-$C_5$ alkylene group or a divalent organic group represented by the formula, —CH=CH—CH=CH—, optionally substituted by $X_n$ to form a cyclic group; R3 is a hydrogen atom or a $C_1$-$C_3$ alkyl group; $R^4$ is a cyano group or a group represented by the formula, —COOR$^5$, —CH$_2$COOR$^5$ or —CONR$^6$R$^7$; and D is a group represented by the formula, —COOR$^8$ or —CONR$^9$R$^{10}$, in which $X_n$ is, same or different, a fluorine atom, a chlorine atom, a bromine atom, an iodine atom, a $C_1$-$C_4$ alkyl group, a $C_1$-$C_4$ alkoxy group, a hydroxyl group, a nitro group or an amino group and n is 0, 1, 2, 3 or 4, $R^5$ is a hydrogen atom or a $C_1$-$C_6$ alkyl group, $R^6$ and $R^7$ are, same or different, a hydrogen atom or a $C_1$-$C_4$ alkyl group, $R^8$ is a hydrogen atom or a $C_1$-$C_6$ alkyl group, $R^9$ and $R^{10}$ are, same or different, a hydrogen atom, a $C_1$-$C_4$ alkyl group or together represent a $C_3$-$C_5$ alkylene group optionally substituted by a methyl group, or physiologically acceptable salts thereof, and an insert carrier or diluent.

2. The plant growth regulator according to claim 1, wherein $R^1$ and $R^2$ are, same or different, a hydrogen atom, a fluorine atom, a chlorine atom, a $C_1$-$C_3$ alkyl group or together represent a $C_3$-$C_5$ alkylene group or a divalent organic group represented by the formula, —CH=CH—CH=CH—, optionally substituted by $X_n$ so as to form a cyclic group; $R^3$ is a hydrogen atom or a $C_1$-$C_3$ alkyl group; $R^4$ is a cyano group or a group represented by the formula, —COOR$^5$ or —CH$_2$COOR$^5$; and D is a group represented by the formula, —COOR$^8$ or —CONR$^9$R$^{10}$, in which $X_n$ is the same or different, a fluorine atom, a chlorine atom, a bromine atom, an iodine atom, a $C_1$-$C_4$ alkyl group, a $C_1$-$C_4$ alkoxy group, a hydroxyl group, a nitro group or an amino group and n is 0, 1, 2, 3 or 4, $R^5$ is a hydrogen atom or a $C_1$-$C_6$ alkyl group, $R^8$ is a hydrogen atom or a $C_1$-$C_4$ alkyl group, $R^9$ and $R^{10}$ are the same or different, a hydrogen atom or a $C_1$-$C_3$ alkyl group, or physiologically acceptable salts thereof, and an inert carrier or diluent.

3. The plant growth regulator according to claim 1 having the formula:

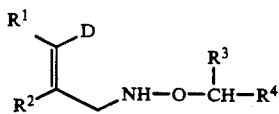

wherein $R^1$ and $R^2$ are, same or different, a hydrogen atom, a chlorine atom, a $C_1$ alkyl group or together represent, a $C_4$ alkylene group or a divalent organic group represented by the formula, —CH=CH—CH=CH—, optionally substituted by $X_n$ to form a cyclic group; $R^3$ is a hydrogen atom or a $C_1$ alkyl group; $R^4$ is a cyano group or a group represented by the formula, —COOR$^5$ or —CH$_2$ COOR$^5$; and D is a group represented by the formula —COOR$^8$ or —CONR$^9$R$^{10}$, in which $X_n$ is, same or different, a fluorine atom, a chlorine atom, a $C_1$ alkyl group, a $C_1$ alkoxy group, a hydroxyl group or a nitro group and n is 0, 1, 2, 3 or 4, $R^5$ is a hydrogen atom or a $C_1$-$C_4$ alkyl group, $R^8$ is a hydrogen atom or a $C_1$-$C_2$ alkyl group, $R^9$ and $R^{10}$ are, same or different, a hydrogen atom or a $C_1$-$C_2$ alkyl group, or physiologically acceptable salts thereof, and an inert carrier or diluent.

4. The plant growth regulator according to claim 1, wherein $R^1$ and $R^2$ are, same or different, a chlorine atom, a $C_1$ alkyl group or a divalent organic group represented by the formula, —CH=CH—CH=CH—, so as to form a cyclic group; $R^3$ is a hydrogen atom or a $C_1$ alkyl group; $R^4$ is a cyano group or a group represented by the formula, —COOR$^5$; and D is a group represented by the formula, —COOR$^8$, in which $R^5$ is a hydrogen atom or a $C_1$ alkyl group, $R^8$ is a hydrogen atom or a $C_1$-$C_2$ alkyl group, or physiologically acceptable salts thereof.

5. The plant growth regulator according to claim 1, wherein $R^1$ and $R^2$ are, same or different, a hydrogen atom, a fluorine atom, a chlorine atom, a bromine atom, an iodine atom, a $C_1$-$C_3$ alkyl group of together represent a $C_3$-$C_5$ alkylene group or a divalent organic group represented by the formula, —CH=CH—CH=CH—, optionally substituted by $X_n$ to form a cyclic group; $R^3$ is a hydrogen atom or a $C_1$-$C_3$ alkyl group; $R^4$ is a cyano group or a group represented by the formula, —COOR$^5$, —CH$_2$COOR$^5$ or —CONR$^6$R$^7$; and D is a group represented by the formula, —COOR$^8$ or —CONR$^9$R$^{10}$, in which $X_n$ is, same or different, a fluorine atom, a chlorine atom, a bromine atom, an iodine atom, a $C_1$-$C_4$ alkyl group, a $C_1$-$C_4$ alkoxy group, a hydroxyl group, a nitro group or an amino group and n is 0, 1, 2, 3 or 4, $R^5$ is a hydrogen atom or a $C_1$-$C_6$ alkyl group, $R^6$ and $R^7$ are, same or different, a hydrogen atom or a $C_1$-$C_4$ alkyl group optionally substituted by a methyl group, $R^8$ is a hydrogen atom or a $C_1$-$C_6$ alkyl group, $R^9$ and $R^{10}$ are, same or different, a hydrogen atom, a $C_1$-$C_4$ alkyl group or together represent a $C_3$-$C_5$ alkylene group optionally substituted by a methyl group, or physiologically acceptable salts thereof, and an inert carrier or diluent.

6. The plant growth regulator according to claim 1, wherein a plant growth regulator is a plant growth regulator utilizing an action of lowering the content of endogenous ethylene in a plant.

7. The plant growth regulator according to claim 1, wherein a plant growth regulator is a plant growth regulator utilizing an action of maintaining the freshness of cut flowers.

8. A method of regulating plant growth, which comprises applying an effective amount of a substituted dicarboxylic acid derivative having the formula:

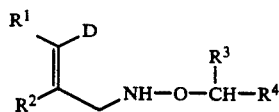

wherein $R^1$ and $R^2$ are, same or different, a hydrogen atom, a fluorine atom, a chlorine atom, a bromine atom, an iodine atom, a $C_1$-$C_3$ alkyl group or together represent a $C_3$-$C_5$ alkylene group or a divalent organic group represented by the formula, —CH=CH—CH=CH—, optionally substituted by $X_n$ to form a cyclic group; $R^3$ is a hydrogen atom or a $C_1$-$C_3$ alkyl group; $R^4$ is a cyano group or a group represented by the formula, —COOR$^5$, —CH$_2$COOR$^5$ or —CONR$^6$R$^7$; and D is a group represented by the formula, —COOR$^8$ or —CONR$^9$R$^{10}$, in which $X_n$ is, same or different, a fluorine atom, a chlorine atom, a bromine atom, an iodine atom, a $C_1$-$C_4$ alkyl group, a $C_1$-$C_4$ alkoxy group, a hydroxyl group, a nitro group or an amino group and n is 0, 1, 2, 3 or 4, $R^5$ is a hydrogen atom or a $C_1$-$C_6$ alkyl group, $R^6$ and $R^7$ are, same or different, a hydrogen atom or a $C_1$-$C_4$ alkyl group $R^8$ is a hydrogen atom or a $C_1$-$C_6$ alkyl group, $R^9$ and $R^{10}$ are the same or different, a hydrogen atom, a $C_1$-$C_4$ alkyl group or together represent a $C_3$-$C_5$ alkylene group optionally substituted by a methyl group, or physiologically acceptable salts thereof.

9. The method according to claim 8, wherein the regulating of plant growth comprises lowering the content of endogenous ethylene in a plant.

10. The method according to claim 8, wherein the regulating of plant growth comprises maintaining the freshness of cut flowers.

11. A substituted dicarboxylic acid derivative having the formula:

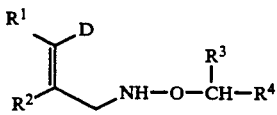

wherein $R^1$ and $R^2$ are, same or different, a hydrogen atom, a fluorine atom, a chlorine atom, a bromine atom, an iodine atom, a $C_1$-$C_3$ alkyl group or together represent a $C_3$-$C_5$ alkylene group or a divalent organic group represented by the formula, —CH=CH—CH=CH—, optionally substituted by $X_n$ to form a cyclic group; $R^3$ is a hydrogen atom or a $C_1$-$C_3$ alkyl group; $R^4$ is a cyano group or a group represented by the formula, —COOR$^5$, —CH$_2$COOR$^5$ or —CONR$^6$R$^7$; and D is a group represented by the formula, —COOR$^8$ or —CONR$^9$R$^{10}$, in which $X_n$ is, same or different, a fluorine atom, a chlorine atom, a bromine atom, an iodine atom, a $C_1$-$C_4$ alkyl group, a $C_1$-$C_4$ alkoxy group, a hydroxyl group, a nitro group or an amino group and n is 0, 1, 2, 3 or 4, $R^5$ is a hydrogen atom or a $C_1$-$C_6$ alkyl group, $R^6$ and $R^7$ are, same or different, a hydrogen atom or a $C_1$-$C_4$ alkyl group $R^8$ is a hydrogen atom or a $C_1$-$C_6$ alkyl group, $R^9$ and $R^{10}$ are, the same or different, a hydrogen atom, a $C_1$-$C_4$ alkyl group or they may together represent a $C_3$-$C_5$ alkylene group optionally substituted by a methyl group, or physiologically acceptable salts thereof, with the proviso that $R^1$ and $R^2$ are not both a hydrogen atom, when $R^4$ is a group represented by the formula —COOR$^5$, D is a group represented by the formula —COOR$^8$, and $R^5$ is a hydrogen atom or a $C_1$-$C_6$ alkyl group.

12. A substituted dicarboxylic acid derivative having the formula:

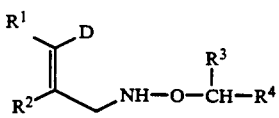

wherein $R^1$ and $R^2$ are, same or different, a fluorine atom, a chlorine atom, a bromine atom, an iodine atom, a $C_1$-$C_3$ alkyl group or together represent a $C_3$-$C_5$ alkylene group or a divalent organic group represented by the formula, —CH=CH—CH=CH—, optionally substituted by $X_n$ so as to form a cyclic group; $R^3$ is a hydrogen atom or a $C_1$-$C_3$ alkyl group; $R^4$ is a cyano group or a group represented by the formula, —COOR$^5$, —CH$_2$COOR$^5$ or —CONR$^6$R$^7$; and D is a group represented by the formula, —COOR$^8$ or —CONR$^9$R$^{10}$, in which $X_n$ is, same or different, a fluorine atom, a chlorine atom, a bromine atom, an iodine atom, a $C_1$-$C_4$ alkyl group, a $C_1$-$C_4$ alkoxy group, a hydroxyl group, a nitro group or an amino group and n is 0, 1, 2, 3 or 4, $R^5$ is a hydrogen atom or a $C_1$-$C_6$ alkyl group, $R^6$ and $R^7$ are, same or different, a hydrogen atom or a $C_1$-$C_4$ alkyl group $R^8$ is a hydrogen atom or a $C_1$-$C_6$ alkyl group, $R^9$ and $R^{10}$ are, same or different, a hydrogen atom, a $C_1$-$C_4$ alkyl group or together represent a $C_3$-$C_5$ alkylene group optionally substituted by a methyl group, or physiologically acceptable salts thereof.

13. A substituted dicarboxylic acid derivative having the formula:

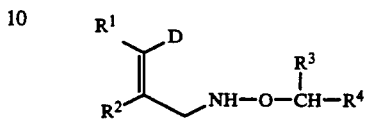

wherein $R^1$ and $R^2$ together represent a divalent organic group represented by the formula, —CH=CH—CH=CH—, to form a cyclic group; $R^3$ is a hydrogen atom or a $C_1$-$C_3$ alkyl group; $R^4$ is a cyano group or a group represented by the formula, —COOR$^5$, —CH$_2$COOR$^5$ or —CONR$^6$R$^7$; and D is a group represented by the formula, —COOR$^8$ or —CONR$^9$R$^{10}$, in which $R^5$ is a hydrogen atom or a $C_1$-$C_5$ alkyl group, $R^6$ and $R^7$ are, same or different, a hydrogen atom or a $C_1$-$C_4$ alkyl group $R^8$ is a hydrogen atom or a $C_1$-$C_6$ alkyl group, $R^9$ and $R^{10}$ are, same or different, a hydrogen atom, a $C_1$-$C_4$ alkyl group or together represent a $C_3$-$C_5$ alkylene group optionally substituted by a methyl group, or physiologically acceptable slats thereof.

14. A substituted dicarboxylic acid derivative having the formula:

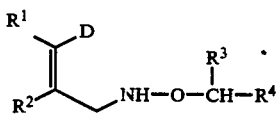

wherein $R^1$ and $R^2$ are, same or different, a hydrogen atom, a fluorine atom, a chlorine atom, a bromine atom, an iodine atom, a $C_1$-$C_3$ alkyl group or together represent a $C_3$-$C_5$ alkylene group or a divalent organic group represented by the formula, —CH=CH—CH=CH—, substituted by $X_n$ to form a cyclic group; $R^3$ is a hydrogen atom or a $C_1$-$C_3$ alkyl group; $R^4$ is a cyano group or a group represented by the formula, —COOR$^5$, —CH$_2$COOR$^5$ or —CONR$^6$R$^7$; and D is a group represented by the formula, —COOR$^8$ or —CONR$^9$R$^{10}$, in which $X_n$ is, same or different, a fluorine atom, a chlorine atom, a bromine atom, an iodine atom, a $C_1$-$C_4$ alkyl group, a $C_1$-$C_4$ alkoxy group, a hydroxyl group, a nitro group or an amino group and n is 1, 2, 3 or 4, $R^5$ is a hydrogen atom or a $C_1$-$C_6$ alkyl group, $R^6$ and $R^7$ are, same or different, a hydrogen atom or a $C_1$-$C_4$ alkyl group $R^8$ is a hydrogen atom or a $C_1$-$C_6$ alkyl group, $R^9$ and $R^{10}$ are, same or different, a hydrogen atom, a $C_1$-$C_4$ alkyl group or together represent a $C_3$-$C_5$ alkylene group optionally substituted by a methyl group, or physiologically acceptable salts thereof, with the proviso that $R^1$ and $R^2$ are not both a hydrogen atom when $R^4$ is a group represented by the formula —COOR$^5$, D is a group represented by the formula —COOR$^8$, and $R^5$ is a hydrogen atom or a $C_1$-$C_6$ alkyl group.

15. A substituted dicarboxylic acid derivative having the formula:

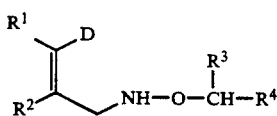

wherein $R^1$ and $R^2$ are, same or different, a hydrogen atom, a fluorine atom, a chlorine atom, a bromine atom, an iodine atom, a $C_1$-$C_3$ alkyl group or together represent a $C_3$-$C_5$ alkylene group or a divalent organic group represented by the formula, —CH=CH—CH=CH—, substituted by $X_n$ to form a cyclic group; $R^3$ is a hydrogen atom or a $C_1$-$C_3$ alkyl group; $R^4$ is a cyano group or a group represented by the formula, —$CH_2COOR^5$ or —$CONR^6R^7$; and D is a group represented by the formula, —$COOR^8$, in which $X_n$ is, same or different, a fluorine atom, a chlorine atom, a bromine atom, an iodine atom, a $C_1$-$C_4$ alkyl group, a $C_1$-$C_4$ alkoxy group, a hydroxyl group, a nitro group or an amino group and n is 1, 2, 3 or 4, $R^5$ is a hydrogen atom or a $C_1$-$C_6$ alkyl group, $R^6$ and $R^7$ are, same or different, a hydrogen atom or a $C_1$-$C_4$ alkyl group $R^8$ is a hydrogen atom or a $C_1$-$C_6$ alkyl group, or physiologically acceptable slats thereof.

16. A substituted dicarboxylic acid derivative having the formula:

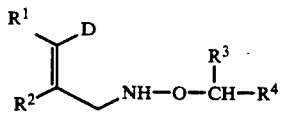

wherein $R^1$ and $R^2$ are, same or different, a hydrogen atom, a fluorine atom, a chlorine atom, a bromine atom, an iodine atom, a $C_1$-$C_3$ alkyl group or together represent a $C_3$-$C_5$ alkylene group or a divalent organic group represented by the formula, —CH=CH—CH=CH—, substituted by $X_n$ to form a cyclic group; $R^3$ is a hydrogen atom or a $C_1$-$C_3$ alkyl group; $R^4$ is a cyano group or a group represented by the formula, —$COOR^5$, —$CH_2COOR^5$ or —$CONR^6R^7$; and D is a group represented by the formula, —$CONR^9R^{10}$, in which $X_n$ is, same or different, a fluorine atom, a chlorine atom, a bromine atom, an iodine atom, a $C_1$-$C_4$ alkyl group, a $C_1$-$C_4$ alkoxy group, a hydroxyl group, a nitro group or an amino group and n is 1, 2, 3 or 4, $R^5$ is a hydrogen atom or a $C_1$-$C_6$ alkyl group, $R^6$ and $R^7$ are, same or different, a hydrogen atom or a $C_1$-$C_4$ alkyl group $R^9$ and $R^{10}$ are, same or different, a hydrogen atom or a $C_1$-$C_4$ alkyl group, or together represent a $C_3$-$C_5$ alkylene group optionally substituted by a methyl group, or physiologically acceptable slats thereof.

17. A substituted dicarboxylic acid derivative having the formula:

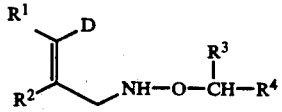

wherein $R^1$ and $R^2$ are, same or different, a fluorine atom, a chlorine atom, a bromine atom, an iodine atom, a $C_1$-$C_3$ alkyl group or together represent a $C_3$-$C_5$ alkylene group as to form a cyclic group; $R^3$ is a hydrogen atom or a $C_1$-$C_3$ alkyl group; $R^4$ is a group represented by the formula, —$COOR^5$; and D is a group represented by the formula, —$COOR^8$, $R^5$ is a hydrogen atom or a $C_1$-$C_6$ alkyl group, $R^8$ is a hydrogen atom or a $C_1$-$C_6$ alkyl group, or physiologically acceptable slats thereof.

18. A substituted dicarboxylic acid derivative having the formula:

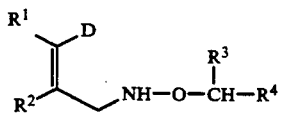

wherein $R^1$ is a hydrogen atom, $R^2$ a fluorine atom, a chlorine atom, a bromine atom, an iodine atom, a $C_1$-$C_3$ alkyl group; $R^3$ is a hydrogen atom or a $C_1$-$C_3$ alkyl group; $R^4$ is a group represented by the formula, —$COOR^5$; and D is a group represented by the formula, —$COOR^8$, $R^5$ is a hydrogen atom or a $C_1$-$C_6$ alkyl group, $R^8$ is a hydrogen atom or a $C_1$-$C_6$ alkyl group, or physiologically acceptable slats thereof.

19. A substituted dicarboxylic acid derivative having the formula:

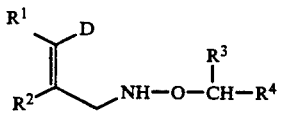

wherein $R^1$ is a fluorine atom, a chlorine atom, a bromine atom, an iodine atom, a $C_1$-$C_3$ alkyl group; $R^2$ is a hydrogen atom, $R^3$ is a hydrogen atom or a $C_1$-$C_3$ alkyl group; $R^4$ is a group represented by the formula, —$COOR^5$; and D is a group represented by the formula, —$COOR^8$, $R^5$ is a hydrogen atom or a $C_1$-$C_6$ alkyl group, $R^8$ is a hydrogen atom or a $C_1$-$C_6$ alkyl group, or physiologically acceptable slats thereof.

20. The plant growth regulator according to claim 1, having the formula

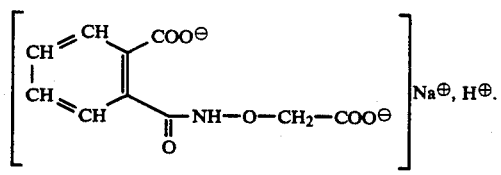

21. A substituted dicarboxylic acid derivative having the formula

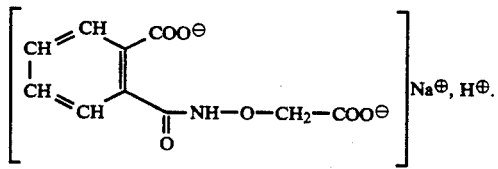

* * * * *

UNITED STATES PATENT AND TRADEMARK OFFICE
CERTIFICATE OF CORRECTION

PATENT NO. : 5,228,899

DATED : 20 July 1993

INVENTOR(S) : Yoshikazu ITOH et al.

It is certified that error appears in the above-identified patent and that said Letters Patent is hereby corrected as shown below:

In claims 1, 3, 8, 11, 12, 13, 14, 15, 16, 17, 18 and 19, at columns 28, 29, 30, 31, 32, 33 and 34, respectively, the formula               should read
--

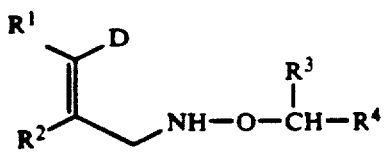          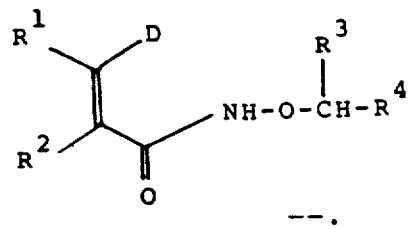

--.

In claim 5, column 30, line 8, "of" should read --or--.

In claim 13, column 32, line 23, "$C_1-C_5$ alkyl" should read --$C_1-C_6$ alkyl--.

In claim 13, column 32, line 30, "slats" should read --salts--.

In claim 15, column 33, line 25, "slats" should read --salts--.

In claim 16, column 33, line 54, "slats" should read --salts--.

In claim 17, column 34, line 7, "slats" should read --salts--.

In claim 18, column 34, line 17, "$R^2$ a" should read --$R^2$ is a--.

UNITED STATES PATENT AND TRADEMARK OFFICE
CERTIFICATE OF CORRECTION

PATENT NO. : 5,228,899
DATED : July 20, 1993
INVENTOR(S) : Yoshikazu Itoh et al

It is certified that error appears in the above-indentified patent and that said Letters Patent is hereby corrected as shown below:

In claim 19, column 34, line 42, "slats" should read --salts--.

Signed and Sealed this

Third Day of May, 1994

Attest:

BRUCE LEHMAN

Attesting Officer    Commissioner of Patents and Trademarks